(12) United States Patent
Ohhashi et al.

(10) Patent No.: US 7,531,604 B2
(45) Date of Patent: May 12, 2009

(54) PHOSPHOLIPID DERIVATIVE

(75) Inventors: Syunsuke Ohhashi, Kanagawa (JP); Kazuhiro Kubo, Kanagawa (JP); Chika Itoh, Kanagawa (JP); Tohru Yasukohchi, Kanagawa (JP); Hiroshi Kikuchi, Tokyo (JP); Norio Suzuki, Chiba (JP); Miho Kurosawa, Shizuoka (JP); Hitoshi Yamauchi, Tokyo (JP)

(73) Assignees: NOF Corporation, Tokyo (JP); Daiichi Pharmaceutical Co., Ltd., Tokyo (JP)

( * ) Notice: Subject to any disclaimer, the term of this patent is extended or adjusted under 35 U.S.C. 154(b) by 615 days.

(21) Appl. No.: 10/529,692
(22) PCT Filed: Sep. 30, 2003
(86) PCT No.: PCT/JP03/12502
§ 371 (c)(1), (2), (4) Date: Dec. 6, 2005
(87) PCT Pub. No.: WO2004/029104
PCT Pub. Date: Apr. 8, 2004

(65) Prior Publication Data
US 2006/0110436 A1 May 25, 2006

(30) Foreign Application Priority Data
Sep. 30, 2002 (JP) .............................. 2002-286306

(51) Int. Cl.
*C08F 8/32* (2006.01)
*C08F 8/40* (2006.01)
*A61K 9/127* (2006.01)
*A61K 47/32* (2006.01)
*A61P 35/00* (2006.01)

(52) U.S. Cl. .............. 525/327.6; 525/329.9; 525/330.5; 525/379; 525/340; 424/450; 424/486; 424/487

(58) Field of Classification Search ............... 525/327.6, 525/329.9, 330.5, 340, 379; 424/450, 486, 424/487
See application file for complete search history.

(56) References Cited

U.S. PATENT DOCUMENTS 5,142,036 A * 8/1992 Akimoto et al. ............ 536/18.3

(Continued)

FOREIGN PATENT DOCUMENTS

EP 0373621 6/1990

(Continued)

OTHER PUBLICATIONS

English language abstract of JP 7-242680, published Sep. 19, 1995.

(Continued)

*Primary Examiner*—Roberto Rábago
(74) *Attorney, Agent, or Firm*—Greenblum & Bernstein P.L.C.

(57) ABSTRACT

A phospholipid derivative, utilizable for modification of liposomes and the like, which is a copolymer containing, as essential component units, a component unit A represented by the formula (1), a component unit B represented by the formula (2A) and/or the formula (2B), and a component unit C represented by the formula (3) [$R^1$ and $R^2$ represent hydrogen atom or methyl group, provided that $R^1$ and $R^2$ do not simultaneously represent methyl group; $R^3$ represents a divalent hydrocarbon group having 1 to 3 carbon atoms; AO represents an oxyalkylene group having 2 to 4 carbon atoms; m represents an average molar number of the added oxyalkylene groups and is a number in the range represented as $4 \leq m \leq 100$; $R^4$ represents hydrogen atom, a hydrocarbon group or acyl group having 1 to 20 carbon atoms; $R^5CO$ and $R^6CO$ represent an acyl group having 8 to 24 carbon atoms; $R^7$ represents a divalent hydrocarbon group having 2 to 4 carbon atoms; and X and Y represent hydrogen atom, an alkali metal atom, ammonium or an organic ammonium] wherein a molar ratio of the component unit A relative to a total of the component unit B and the component unit C is from 7/3 to 3/7, and the component unit C is contained at a ratio of from 1 to 4 moles per 1 mole of the copolymer.

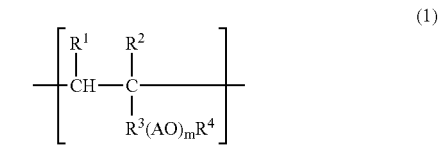

(1)

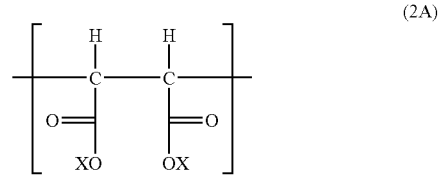

(2A)

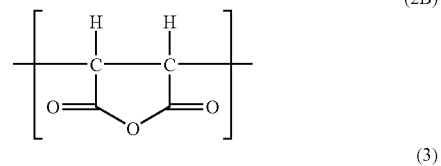

(2B)

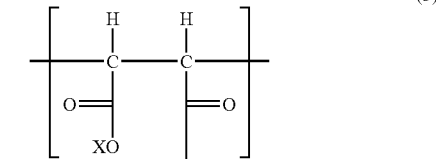

(3)

11 Claims, No Drawings

U.S. PATENT DOCUMENTS

| | | |
|---|---|---|
| 5,173,219 A | 12/1992 | Kim |
| 5,395,619 A | 3/1995 | Zalipsky et al. |
| 5,540,935 A | 7/1996 | Miyazaki et al. |
| 5,631,018 A | 5/1997 | Zalipsky et al. |
| 6,344,576 B1 | 2/2002 | Eibl |
| 6,436,905 B1 | 8/2002 | Tonge et al. |
| 2003/0144247 A1 | 7/2003 | Kuwano et al. |
| 2005/0220856 A1 | 10/2005 | Itoh et al. |
| 2006/0210618 A1 | 9/2006 | Kubo et al. |
| 2007/0031481 A1 | 2/2007 | Itoh et al. |

FOREIGN PATENT DOCUMENTS

| | | |
|---|---|---|
| EP | 0657463 | 6/1995 |
| EP | 1279406 | 1/2003 |
| JP | 63-221837 | 9/1988 |
| JP | 2-163108 | 6/1990 |
| JP | 6-228012 | 8/1994 |
| JP | 7-242680 | 9/1995 |
| JP | 7-268038 | 10/1995 |
| JP | 9-255740 | 9/1997 |
| JP | 2002-522442 | 7/2002 |
| WO | 03/082882 | 10/1993 |
| WO | 99/09955 | 3/1999 |
| WO | WO 99/09955 * | 3/1999 |
| WO | 00/08031 | 2/2000 |
| WO | 00/33817 | 6/2000 |
| WO | 01/05375 | 1/2001 |
| WO | 2004/060899 | 7/2004 |
| WO | 2004/083219 | 9/2004 |

OTHER PUBLICATIONS

English language abstract of JP 2002-522442, published Jul. 23, 2002.
T. Yuda et al., Biological and Pharmaceutical Bulletin, vol. 19, No. 10, pp. 1347-1351, 1996.
R. Zeisig et al., Biochimica et Biophysica Acta, vol. 1285, No. 2, pp. 237-245, 1996.
T.M. Allen et al., Biochimica et Biophysica Acta, vol. 1061, No. 1, pp. 56-64, 1991.
Database WPI, Section Ch, Week 199546, Derwent Publications Ltd., London, GB, AN 1995-355265, XP002354282, 1995.
Biochimica et Biophysica Acta, 1983, vol. 761, pp. 142-151.
Biochemical Pharmacology, 1983, vol. 32 pp. 3381-3387.
The Pharmaceutical Society of Japan, the 106th Annual Meeting Summaries of Symposia, 1986, p. 336.
Febs Letters, 1987, vol. 223, pp. 42-46.
English Language Abstract of JP 63-221837, 1988.
Chemical & Pharmaceutical Bulletin, 1990, vol. 38, pp. 1633-1638.
Biochimica et Biophysica Acta, 1992, vol. 1108, pp. 257-260.
English Language Abstract of JP 6-228012, 1994.
English Language Abstract of JP 2-163108, 1990.
English Language Abstract of JP 9-255740, 1997.
Febs Letter, vol. 268, No. 1, pp. 235-237 (1990).
English Language Abstract of JP 7-268038, 1995.

* cited by examiner

PHOSPHOLIPID DERIVATIVE

TECHNICAL FIELD

The present invention relates to a phospholipid derivative. More specifically, the present invention relates to a phospholipid derivative obtainable by reacting an alkenyl ether/maleic anhydride copolymer with a phospholipid.

BACKGROUND ART

Microparticle drug carriers including liposomal drug as typical examples and polypeptides such as protein drug are known to have poor retention in blood and be easily captured by the reticuloendothelial system (hereinafter abbreviated as "RES") such as liver and spleen when they are intravenously administered. The presence of RES is a serious obstacle when a microparticle drug carrier is utilized as a targeting type preparation, which delivers a medicament to organs other than RES, and as a sustained-release preparation, which allows a medicament retained in blood for a long period of time to control the release of the medicament.

Researches have so far been conducted to provide a microcirculation property to the aforementioned preparations. Some proposals have been made, including, for example, maintenance of a high blood concentration by reducing a size of liposomes in view of relative easiness of a control of physicochemical properties of lipid bilayers of liposomes (Biochimica et Biophysica Acta, Vol. 761, p. 142, 1983), utilization of lecithin having a high phase transfer temperature (Biochemical Pharmacology, Vol. 32, p. 3381, 1983), utilization of sphingomyelin instead of lecithin (Biochemical Pharmacology, Vol. 32, p. 3381, 1983), addition of cholesterol as a membrane component of liposomes (Biochimica et Biophysica Acta, Vol. 761, p. 142, 1983) and the like.

As another approach for solution, research has been made for providing a microcirculation property and escapability from RES by modification of membrane surfaces of liposomes with a glycolipid, glycoprotein, amino acid-lipid, polyethylene glycol-lipid or the like. Substances for the modification so far reported include, for example, glycophon (The Pharmaceutical Society of Japan, the 106th Annual Meeting, Summaries of Symposia, p. 336, 1986), ganglioside GM1 (FEBS Letters, Vol. 223, p. 42, 1987), phosphatidylinositol (FEBS Letters, Vol. 223, p. 42, 1987), glycophon and ganglioside GM3 (Japanese Patent Unexamined Publication (Kokai) No. 63-221837), polyethylene glycol derivative (FEBS Letters, Vol. 268, p. 236, 1990), glucuronic acid derivative (Chemical & Pharmaceutical Bulletin, Vol.38, p. 1633, 1990), glutamic acid derivative (Biochimica et Biophysica Acta, Vol.1108, p. 257, 1992), polyglycerin phospholipids derivative (Japanese Patent Unexamined Publication No. 6-228012), and the like.

As the modification of a polypeptide, introduction of two water-soluble polymer molecules into a polypeptide by using triazine has been reported for a purpose of decreasing the number of binding sites of the polypeptide and thereby increasing a residual amount of active groups such as lysine residues in the polypeptide. Also as for a liposome preparation, introduction of two water-soluble polymer molecules into triazine to increase the molecular weight of the water-soluble polymer, and modification of liposome surfaces by using the resulting polymer is reported. However, when a water-soluble polymer is introduced by using triazine, only two water-soluble polymers can be introduced into the triazine ring. Therefore, it is necessary to add a large amount of a compound, which contains two water-soluble polymers introduced in triazine, to increase the number of the water-soluble polymer chains on liposome surfaces.

However, in the above approach, a problem arises in that reactive sites to be primarily reacted with a medicament are consumed due to the addition of a large amount of the compound, and accordingly, a type of pharmaceutical preparation to be desired is limited.

DISCLOSURE OF THE INVENTION

An object of the present invention is to provide a phospholipid derivative that can be utilized for modification of liposomes or the like. The inventors of the present invention conducted various researches to provide a novel phospholipid derivative by reacting an alkenyl ether/maleic anhydride copolymer with a phospholipid, and successfully provided the following phospholipid.

The present invention thus provides a phospholipid derivative, which is a copolymer containing, as essential component units, (A) a component unit A represented by the following formula (1), (B) a component unit B represented by the following formula (2A) and/or the following formula (2B), and (C) a component unit C represented by the following formula (3):

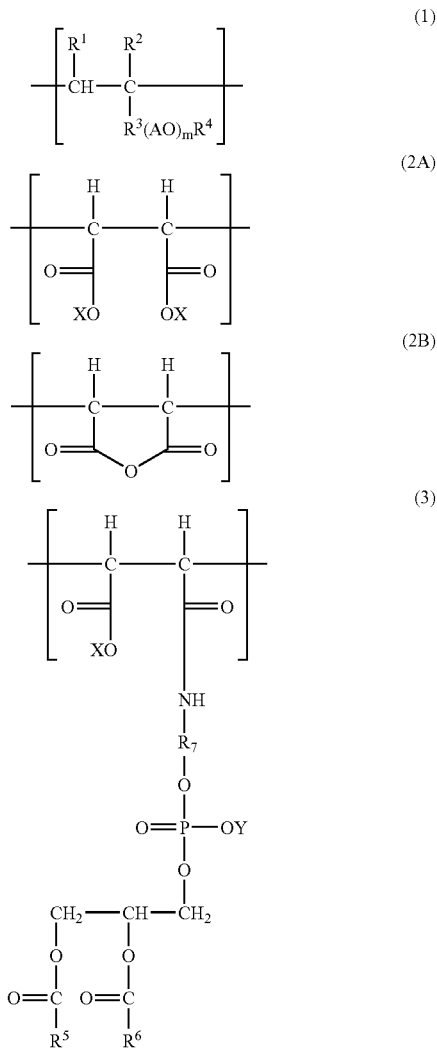

wherein, in the formula (1), $R^1$ and $R^2$ independently represent hydrogen atom or methyl group, provided that $R^1$ and $R^2$ do not simultaneously represent methyl group; $R^3$ represents a divalent hydrocarbon group having 1 to 3 carbon atoms; AO independently represents an oxyalkylene group having 2 to 4 carbon atoms; m represents an average molar number of added oxyalkylene groups and is a number in a range of $4 \leqq m \leqq 100$; and $R^4$ represents hydrogen atom, a hydrocarbon group having 1 to 20 carbon atoms, or an acyl group having 1 to 20 carbon atoms; in the formula (2A), X independently represents hydrogen atom, an alkali metal atom, ammonium or an organic ammonium; and in the formula (3), $R^5CO$ and $R^6CO$ independently represent an acyl group having 8 to 24 carbon atoms; $R^7$ represents a divalent hydrocarbon group having 2 to 4 carbon atoms; X represents hydrogen atom, an alkali metal atom, ammonium, or an organic ammonium; and Y represents hydrogen atom, an alkali metal atom, ammonium or an organic ammonium, wherein a molar ratio of the component unit A relative to the total of the component unit B and the component unit C is 7/3 to 3/7, and the component unit C is contained at a ratio of 1 to 5 moles per 1 mole of said copolymer.

According to preferred embodiments, the present invention provides the aforementioned phospholipid derivative, wherein the total number of the component unit(s) A, the component unit(s) B, and the component unit(s) C contained in the copolymer is 3 or more and 150 or less; the aforementioned phospholipid derivative, wherein the total number of the component unit(s) A, the component unit(s) B, and the component unit(s) C contained in the copolymer is 5 or more and 50 or less; the aforementioned phospholipid derivative, wherein $R^1$ and $R^2$ represent hydrogen atom; and the aforementioned phospholipid derivative, wherein $R^7$ represents ethylene group.

From other aspects, the present invention provides a surfactant comprising the aforementioned phospholipid derivative; a solubilizer comprising the aforementioned phospholipid derivative; a dispersing agent, preferably a dispersing agent for cosmetics, comprising the aforementioned phospholipid derivative; and a lipid membrane structure, preferably a liposome, containing the aforementioned phospholipid derivative. The present invention also provides the aforementioned lipid membrane structure or liposome retaining a medicament, and as a preferred embodiment thereof, the aforementioned lipid membrane structure or liposome retaining an antitumor agent.

From a further aspect, the present invention provides a method for producing the aforementioned phospholipid derivative, which comprises the step of reacting a copolymer containing the component unit A and the component unit B at a molar ratio of 7/3 to 3/7 with a compound represented by the following formula (4):

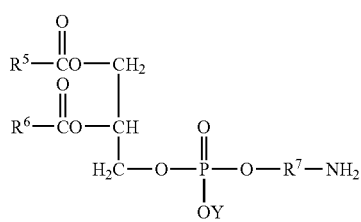

(4)

wherein $R^5CO$, $R^6CO$, $R^7$ and Y have the same meanings as those defined above.

BEST MODE FOR CARRYING OUT THE INVENTION

The phospholipid derivative of the present invention is characterized to be a copolymer containing the component unit A represented by the formula (1) derived from an alkenyl ether, and the component unit B represented by the formula (2A) and/or the formula (2B) derived from maleic acid or a salt thereof or maleic anhydride, and further containing the component unit C represented by the formula (3) having a residue of a phospholipid compound.

$R^1$ and $R^2$ independently represent hydrogen atom or methyl group, provided that $R^1$ and $R^2$ do not simultaneously represent methyl group. It is preferred that $R^1$ represents hydrogen atom, $R^2$ represents hydrogen atom or methyl group, and $R^3$ represents methylene group. $R^3$ represents a divalent hydrocarbon group having 1 to 3 carbon atoms, and specific examples thereof include hydrocarbon groups of —CH$_2$—, —CH$_2$CH$_2$—, —CH(CH$_3$)CH$_2$—, —CH$_2$CH$_2$CH$_2$— and the like. Among them, —CH$_2$— (methylene group) is preferred.

The oxyalkylene group represented by AO is an oxyalkylene group having 2 to 4 carbon atoms, and examples thereof include oxyethylene group, oxypropylene group, oxytrimethylene group, oxybutylene group, oxytetramethylene group and the like. Among them, oxyethylene group and oxypropylene group are preferred, and oxyethylene group is particularly preferred. The oxyalkylene group represented by AO, having 2 to 4 carbon atoms, of which an average number of added moles is 'm' may consist of one or more kind of oxyalkylene groups. When two or more kinds of oxyalkylene groups are contained, combination thereof is not limited, and the polyoxyalkylene group may be a block or random copolymer. The component unit A preferably contains oxyethylene group as the oxyalkylene group represented by AO, and a ratio of the oxyethylene group may preferably be more than 50 to 100% by mass, more preferably 70 to 100% by mass, further preferably 100% by mass, in the oxyalkylene groups. When a ratio of the oxyethylene group is less than 50% by mass, lipophilicity of the phospholipid derivative is increased, and thus emulsifying and dispersing properties of the copolymer may sometimes be degraded.

Symbol "m" is an average molar number of added oxyalkylene groups, and m may be a number of from 4 to 100, preferably from 6 to 46. When m is smaller than 4, the length of the polyoxyalkylene chain becomes relatively short, as compared to the size of the copolymer, to give reduction of water-solubility of the copolymer, which may sometimes result in lowering of the effect of the phospholipid derivative when used as a drug delivery system. Further, when m is larger than 100, the number of the polyalkylene glycol chains comprising the oxyalkylene groups becomes relatively small, which may sometimes results in reduction of the advantages of the phospholipid derivative when used as a drug delivery system.

$R^4$ represents hydrogen atom or a hydrocarbon group or an acyl group having 1 to 20 carbon atoms. Examples of the hydrocarbon group include an aliphatic hydrocarbon group having 1 to 20 carbon atoms and an aromatic hydrocarbon group having 1 to 20 carbon atoms. Examples of the aliphatic hydrocarbon group having 1 to 20 carbon atoms include methyl group, ethyl group, propyl group, isopropyl group, butyl group, isobutyl group, tert-butyl group, pentyl group, isopentyl group, hexyl group, isoheptyl group, 2-ethylhexyl group, octyl group, isononyl group, decyl group, dodecyl group, isotridecyl group, tetradecyl group, hexadecyl group, isocetyl group, octadecyl group, isostearyl group, octadecenyl group, octyldodecyl group, docosyl group, decyltetradecyl group and the like. Examples of the aromatic hydrocarbon group having 1 to 20 carbon atoms include benzyl group, tolyl group, butylphenyl group, dibutylphenyl group, octylphenyl group, nonylphenyl group, dodecylphenyl group, dioctylphenyl group, dinonylphenyl group and the like.

Example of the acyl group having 1 to 20 carbon atoms include an acyl group derived from acetic acid, propionic acid, butyric acid, isobutyric acid, caprylic acid, 2-ethylhexanoic acid, isononanoic acid, capric acid, lauric acid, myristic acid, palmitic acid, isopalmitic acid, stearic acid, isostearic acid, arachic acid, behenic acid, palmitoleic acid, oleic acid, linoleic acid, linolenic acid, erucic acid, benzoic acid, hydroxybenzoic acid, cinnamic acid, gallic acid, and the like. $R^4$ preferably represents a hydrocarbon group or acyl group having 1 to 4 carbon atoms, and a hydrocarbon group having 1 to 4 carbon atoms is more preferred. The groups of $R^4$ in the component units A represented by the formula (1) are independent from one another, and may consist of one or more types of groups.

The component units represented by the formula (2A), (2B), and (3) are component units derived from maleic acid or a salt thereof or maleic anhydride. Examples of the salt include a salt of alkali metal atom, ammonium or an organic ammonium, for example, a salt of an alkali metal such as sodium and potassium, a salt of an alkali metal such as calcium and magnesium, an ammonium salt derived from ammonium, a salt of an organic ammonium salt derived from triethylamine, pyridine or dimethylaminopyridine. Maleic acid or a salt thereof or maleic anhydride may be copolymerized without pretreatment, or maleic acid may be copolymerized and then converted into a salt.

$R^5CO$ and $R^6CO$ independently represent an acyl group having 8 to 24 carbon atoms. As this acyl group, an acyl groups derived from an ordinary fatty acid can be used. Examples of $R^5CO$ and $R^6CO$ include an acyl group derived from a saturated or unsaturated linear or branched fatty acid such as caprylic acid, capric acid, lauric acid, myristic acid, palmitic acid, palmitoleic acid, stearic acid, isostearic acid, oleic acid, linoleic acid, arachic acid, behenic acid, erucic acid, and lignoceric acid. $R^5CO$ and $R^6CO$ contained in one component unit may be the same or different. Further, $R^5CO$ and $R^6CO$ in each component unit are independently selected and may consist of one or more kinds of groups. $R^5CO$ and $R^6CO$ preferably represent an acyl group having 10 to 22 carbon atoms. When the number of carbon atoms exceeds 24, reactivity may sometimes be degraded due to poor dispersion in an aqueous phase. When the number of carbon atoms is less than 8, purity may sometimes be degraded due to poor crystallizing property during a purification process.

X represents hydrogen atom or a salt of alkali metal atom, ammonium or an organic ammonium, and examples include, for example, a salt of an alkali metal such as sodium and potassium, a salt of an alkali metal such as calcium and magnesium, an ammonium salt derived from ammonium, an organic ammonium salt derived from triethylamine, pyridine, or dimethylaminopyridine. Y represents hydrogen atom, an alkali metal atom, ammonium or an organic ammonium, preferably, hydrogen atom or an alkali metal atom. More specifically, examples of the alkali metal atom include sodium and potassium, and examples of the organic ammonium include organic ammonium derived from triethylamine and the like. $R^7$ represents a divalent hydrocarbon group having 2 to 4 carbon atoms. More specifically, examples thereof include hydrocarbon groups of $-CH_2CH_2-$, $-CH(CH_3)CH_2-$, $-CH_2CH_2CH_2-$, $-CH_2CH_2CH_2CH_2-$, $-CH(CH_3)CH_2CH_2-$, $-CH_2CH(CH_3)CH_2-$, $-CH(CH_2CH_3)CH_2-$ and the like, and ethylene group represented by $-CH_2CH_2-$ is preferred.

In the phospholipid derivative of the present invention, the total number of the component unit(s) A represented by the formula (1), the component unit(s) B represented by the formula (2A) and/or formula (2B) (the component units B may consist solely of component unit(s) represented by the formula (2A) or (2B), or may contain both of the component units represented by the formula (2A) and formula (2B)) and the component unit(s) C represented by the formula (3) contained in the copolymer is 3 or more and 150 or less. When the molar number of the component unit A is represented by $k^I$, the molar number of the component unit B is represented by $k^{II}$, and the molar number of the component unit C is represented by $k^{III}$, $k^I$, $k^{II}$ and $k^{III}$ should satisfy the following relationships: $1 \leq k^{III} \leq 5$, $3 \leq k^I + k^{II} + k^{III} \leq 150$, $k^I/(k^{II}+k^{III}) = 7/3$ to $3/7$, preferably, the following relationships: $1 \leq k^{III} \leq 4$, $5 \leq k^I + k^{II} + k^{III} \leq 100$, $k^I/(k^{II}+k^{III}) = 6/4$ to $4/6$, more preferably, the following relationships: $1 \leq k^{III} \leq 2$, $5 \leq k^I + k^{II} + k^{III} \leq 100$, $k^I/(k^{II}+k^{III}) = 6/4$ to $4/6$. The end of the molecule of the phospholipid derivative of the present invention is hydrogen atom or a residue that binds to the copolymer end by polymerization initiation or chain transfer. It is preferred that the component units C exists in the molecule in a random manner.

The phospholipid derivative of the present invention may contain component units derived from other monomers copolymerizable with the component units A, B, and C in addition to these component units. Examples of the copolymerizable monomers include styrene, vinyl acetate, acrylonitrile, methacrylonitrile, acrylamide, methacrylamide, acrylic acid, methacrylic acid, methyl acrylate, methyl methacrylate and the like. A ratio of the component units derived from other copolymerizable monomers is preferably 10% by mole or less based on the component unit A.

The phospholipid derivative of the present invention can be produced by reacting a phospholipid compound represented by the aforementioned formula (4) with a copolymer containing the component unit A and the component unit B. The copolymer containing the component unit A and the component unit B is a known polymer and can be prepared by a known method (for example, the methods described in Japanese Patent Unexamined Publication Nos. 2-163108, 9-255740 and the like). The copolymer can be prepared by, for example, performing solution polymerization of a suitable monomer providing the component unit A and maleic acid or a salt thereof or maleic anhydride in an organic solvent or aqueous solvent, or bulk polymerization thereof without using a solvent. Solution polymerization in an organic solvent and bulk polymerization without using a solvent are preferred, and bulk polymerization without using a solvent is more preferred. In the copolymer, although the component units A represented by the formula (I) may exist in the polymer either in a random or block manner, they preferably exist in a random manner. Further, although the component units represented by the formula (2A) and/or formula (2B) may also exist in the polymer either in a random or block manner, they preferably exist in a random manner.

When the component unit B is derived from maleic anhydride, and polymerization using an organic solvent or bulk polymerization without using a solvent is performed, the component unit B in the copolymer can be obtained as a component unit represented by the formula (2B). When polymerization is performed in an aqueous solvent, the component unit B can be obtained as a component unit derived from maleic acid or a salt thereof (the component unit represented by the formula (2A)). In the aforementioned reaction, when the component unit B is either of an anhydride or carboxylic acid or a salt thereof, the phospholipid can be introduced.

Examples of a polymerization initiator used in the polymerization reaction include a peroxide initiator such as benzoyl peroxide, azo initiator such as 2,2'-azobisisobutyronitrile, and the like. An amount to be charged may usually be 0.001 to 0.1% by mole, preferably 0.005 to 0.1% by mole, based on the total charge amount of the monomers. Further, the polymerization can be performed by using a chain transfer agent in combination, if necessary. As for the reaction conditions, the reaction is usually performed at a reaction temperature of 0 to 120° C. for a reaction time of 1 to 50 hours, preferably at a reaction temperature of 20 to 100° C. for a reaction time of 2 to 25 hours. A molar ratio of the component unit A and the component unit B constituting the copolymer is 7/3 to 3/7, preferably 6/4 to 4/6, more preferably 5/5. Further, a mass average molecular weight of the copolymer is 10,000 to 1,000,000, preferably 10,000 to 200,000.

When a copolymer containing the component unit A and the component unit B is reacted with a phospholipid compound represented by the aforementioned formula (4), the reaction is preferably performed in the presence of a basic catalyst or a dehydration condensation catalyst. Further, it is also preferable to perform the reaction in an organic solvent. A type of the basic catalyst is not particularly limited, and examples thereof include a nitrogen-containing substance such as triethylamine, pyridine, dimethylaminopyridine and ammonium acetate and an organic salt such as sodium phosphate, sodium carbonate, sodium hydrogencarbonate, sodium borate and sodium acetate. Further, examples of the dehydration condensation catalyst include dicyclohexylcarbodiimide (DCC), 1-ethyl-3-(3-dimethylaminopropyl)carbodiimide hydrochloride and the like. An amount of the catalyst is, for example, 0.5 to 10 moles, preferably 1 to 5 moles, per mole of the aforementioned phospholipid compound. A reaction temperature is usually 20 to 90° C., preferably 40 to 80° C. A reaction time is 1 hour or longer, preferably 2 to 8 hours. If the reaction temperature is lower than 20° C., the reaction rate may sometimes be low. If the reaction temperature is higher than 90° C., the acyl group in the phospholipid compound represented by the formula (4) used for the reaction may sometimes be hydrolyzed.

An amount of addition of the phospholipid compound represented by the formula (4) is 1 to 5 moles, preferably 1 to 4 moles, more preferably 1 to 2 moles, based on the average molecular weight of the copolymer (CP) comprising the component unit A and the component unit B. If the addition amount of the phospholipid compound is too large, preparation of liposomes may sometimes become difficult due to increase in phospholipid that binds to the copolymer, and preparation of micelles may sometimes become difficult when used as a surfactant. Further, if the addition amount of the phospholipid compound is too small, a ratio of lipophilic groups becomes too small for a surfactant, and thus preparation of micelles by an action as a surfactant may not be expected.

The phospholipid derivative of the present invention enables solubilization, emulsification or dispersion as a surfactant for a fat-soluble substance, or can be used as a surfactant in the field of cosmetics, and it can also be used as a phospholipid for formulating a lipid membrane structure. The lipid membrane structure is preferably used as a liposome. The liposoluble substance that can be solubilized is not particularly limited, and examples thereof include a higher alcohol, ester oil, triglycerin, tocopherol, higher fatty acid and the like. The use as a dispersing agent in the field of cosmetics is also not particularly limited. For example, when a water-soluble substance such as ascorbic acid is retained in a lipid bilayer or the like, the objective substance can be more stably dispersed in an aqueous solution by using the compound of the present invention as a lipid membrane structure forming agent. When the compound is used as a surfactant or a dispersing agent, an amount to be added is 0.1 to 20% by mass, preferably 0.5 to 7% by mass, more preferably 0.5 to 5% by mass, based on a total mass of an objective substance for solubilization, dispersion, emulsification or the like.

Further, the phospholipid derivative of the present invention can be used as a pH sensitive phospholipid, for example, as a dispersing agent. When a cationic substance, for example, a physiologically active cationic substance or a basic substance, is dispersed in water, it can be stably dispersed in water by, for example, coating the surfaces of microparticles or the like containing the cationic substance or basic substance with the aforementioned compound. The phospholipid derivative of the present invention has polyanionic groups, and thereby enables stable dispersion by ionic bonds.

An amount of the phospholipid derivative of the present invention added to a lipid membrane structure may be an amount sufficient for effectively expressing efficacy of a medicament in vivo and is not particularly limited. The amount can be suitably selected depending on, for example, a type of medicament to be retained by the lipid membrane structure, a purpose of therapeutic or prophylactic treatment and the like, and a form of the lipid membrane structure. A type of a medicament retained by the lipid membrane structure provided by the present invention is not particularly limited. For example, compounds used as antitumor agents are preferred. Examples of such compounds include, for example, camptothecin derivatives such as irinotecan hydrochloride, nogitecan hydrochloride, exatecan, RFS-2000, lurtotecan, BNP-1350, Bay-383441, PNU-166148, IDEC-132, BN-80915, DB-38, DB-81, DB-90, DB-91, CKD-620, T-0128, ST-1480, ST-1481, DRF-1042 and DE-310, taxane derivatives such as docetaxel hydrate, paclitaxel, IND-5109, BMS-184476, BMS-188797, T-3782, TAX-1011, SB-RA-31012, SBT-1514 and DJ-927, ifosfamide, nimustine hydrochloride, carboquone, cyclophosphamide, dacarbazine, thiotepa, busulfan, melphalan, ranimustine, estramustine phosphate sodium, 6-mercaptopurine riboside, enocitabine, gemcitabine hydrochloride, carmofur, cytarabine, cytarabine ocphosphate, tegafur, doxifluridine, hydroxycarbamide, fluorouracil, methotrexate, mercaptopurine, fludarabine phosphate, actinomycin D, aclarubicin hydrochloride, idarubicin hydrochloride, epirubicin hydrochloride, daunorubicin hydrochloride, doxorubicin hydrochloride, pirarubicin hydrochloride, bleomycin hydrochloride, zinostatin stimalamer, neocarzinostatin, mytomycin C, bleomycin sulfate, peplomycin sulfate, etoposide, vinorelbine tartrate, vincristine sulfate, vindesine sulfate, vinblastine sulfate, amrubicin hydrochloride, gefitinib, exemestan, capecitabine, TNP-470, TAK-165, KW-2401, KW-2170, KW-2871, KT-5555, KT-8391, TZT-1027, S-3304, CS-682, YM-511, YM-598, TAT-59, TAS-101, TAS-102, TA-106, FK-228, FK-317, E7070, E7389, KRN-700, KRN-5500, J-107088, HMN-214, SM-11355, ZD-0473 and the like.

Further, a gene or the like may be encapsulated in the lipid membrane structure of the present invention. The gene may be any of oligonucleotide, DNA, and RNA, and in particular, examples thereof include a gene for in vitro gene introduction such as transformation and a gene that act upon in vivo expression, for example, a gene for gene therapy, gene used in breeding of industrial animals such as laboratory animals and livestock, and the like. Examples of the gene for gene therapy include an antisense oligonucleotide, antisense DNA, antisense RNA, gene coding for a physiologically active substance such as enzymes and cytokines, and the like.

The aforementioned lipid membrane structure may further contain phospholipids and a sterol such as cholesterol, and cholestanol, another fatty acid having a saturated or unsaturated acyl group having 8 to 24 carbon atoms and an antioxidant such as α-tocopherol. Examples of the phospholipid include phosphatidylethanolamine, phosphatidylcholine, phosphatidylserine, phosphatidylinositol, phosphatidylglycerol, cardiolipin, sphingomyelin, ceramide phosphorylethanolamine, ceramide phosphorylglycerol, ceramide phosphorylglycerol phosphate, 1,2-dimyristoyl- 1,2-deoxyphosphatidylcholine, plasmalogen, phosphatidic acid and the like, and they may be used alone or two or more kind of them can be used in combination. The fatty acid residues of these phospholipids are not particularly limited, and examples thereof include a saturated or unsaturated fatty acid residue having 12 to 20 carbon atoms. Specific examples include an acyl group derived from a fatty acid such as lauric acid, myristic acid, palmitic acid, stearic acid, oleic acid and linoleic acid. Further, phospholipids derived from natural products such as egg yolk lecithin and soybean lecithin can also be used.

The form of the lipid membrane structure of the present invention and the preparation method thereof are not particularly limited, and examples of the existence form thereof include, for example, a form of dried lipid mixture, form of dispersion in an aqueous solvent, dried or frozen form of the foregoing form and the like. The lipid membrane structure in the form of dried lipid mixture can be prepared by, for example, first dissolving lipid components to be used in an organic solvent such as chloroform, and drying up the solution under reduced pressure by using an evaporator or spray-drying the solution by using a spray dryer. Examples of the form of the lipid membrane structure dispersed in an aqueous solvent include unilamella liposomes, multilamella liposomes, O/W type emulsion, W/O/W type emulsion, spherical micelles, worm-like micelles, irregular layered structure and the like, and liposomes are preferred among them. A size of the lipid membrane structure in the dispersed state is not particularly limited. For example, the particle diameter of liposome or particle in emulsion is 50 nm to 5 μm, and the particle diameter of spherical micelle is 5 to 100 nm. When a worm-like micelle or irregular layered structure is formed, it can be considered that the thickness of one layer thereof is 5 to 10 nm, and such layers form a single layer.

The composition of the aqueous solvent (dispersion medium) is also not particularly limited, and the aqueous solvent may be, for example, a buffer such as phosphate buffer, citrate buffer, and phosphate-buffered physiological saline, physiological saline, a medium for cell culture or the like. The lipid membrane structure can be stably dispersed in these aqueous solvents. An aqueous solution of a sugar such as glucose, lactose, and sucrose, an aqueous solution of a polyhydric alcohol such as glycerin and propylene glycol and the like may be further added. In order to stably store the lipid membrane structure dispersed in such an aqueous solvent for a long period of time, it is desirable to minimize electrolytes in the aqueous solvent from a viewpoint of physical stability such as prevention of aggregation. Further, from a viewpoint of chemical stability of lipids, it is desirable to control a pH of the aqueous solvent to be in a range of from weakly acidic pH to around neutral pH (pH 3.0 to 8.0), and to remove dissolved oxygen by nitrogen bubbling. Further, when a lyophilized or spray-dried product is stored, for example, use of an aqueous sugar solution or aqueous polyhydric alcohol solution may enable effective storage at lyophilization and storage of an aqueous sugar solution. A concentration of these aqueous solvents is not particularly limited. When an aqueous sugar solution is used, for example, the concentration is preferably 2 to 20% (W/V), more preferably 5 to 10% (W/V), and when an aqueous polyhydric alcohol solution is used, the concentration is preferably 1 to 5% (W/V), more preferably 2 to 2.5% (W/V). In a buffer, a concentration of the buffering agent is preferably 5 to 50 mM, more preferably 10 to 20 mM. A concentration of the lipid membrane structure in an aqueous solvent is not particularly limited. A concentration of the total amount of lipids in the lipid membrane structure is preferably 0.1 to 500 mM, more preferably 1 to 100 mM.

The form of the lipid membrane structure dispersed in an aqueous solvent can be prepared by adding the aforementioned dried lipid mixture to an aqueous solvent and emulsifying the mixture by using an emulsifier such as a homogenizer, ultrasonic emulsifier, high pressure jet emulsifier or the like. Further, the aforementioned form can also be prepared by a method known as a method for preparing liposomes, for example, the reverse phase evaporation method, and the method for preparing dispersion is not particularly limited. When it is desired to control a size of the lipid membrane structure, extrusion (extrusion filtration) can be performed under high pressure by using a membrane filter of even pore sizes or the like.

Examples of the method for drying the aforementioned lipid membrane structure dispersed in an aqueous solvent include ordinary lyophilization and spray drying. As the aqueous solvent used for these operations, an aqueous sugar solution, preferably aqueous sucrose solution or aqueous lactose solution, may be used as described above. When a lipid membrane structure dispersed in the aqueous solvent is first prepared and then successively dried, it becomes possible to store the lipid membrane structure for a long period of time. In addition, when an aqueous solution of a medicament is added to the dried lipid membrane structure, the lipid mixture is efficiently hydrated and thereby the medicament can be efficiently retained in the lipid membrane structure, which provides an advantageous effect. For example, a pharmaceutical composition can be prepared by adding a medicament to the lipid membrane structure, and thus the lipid membrane structure can be used as a pharmaceutical composition for therapeutic treatment and/or prevention of a disease. When the medicament is a gene, the composition can also be used as a gene delivery kit.

As for a form of the pharmaceutical composition, the form may be the lipid membrane structures retaining a medicament, as well as a mixture of a medicament and the lipid membrane structures. The term "retain" used herein means that a medicament exists inside the membranes of the lipid membrane structures, on the membrane surfaces, in the membranes, in the lipid layers, and/or on the lipid layer surfaces. An available form of the pharmaceutical composition and a method for preparation thereof are not particularly limited in the same manner as the lipid membrane structures. As for the available form, examples include a form of a dried mixture, a form of a dispersion in an aqueous solvent, and forms obtained by further drying or freezing said forms.

A dried mixture of lipids and a medicament can be produced by, for example, once dissolving lipid components and a medicament to be used in an organic solvent such as chloroform and then subjecting the resulting solution to solidification under reduced pressure by using an evaporator or spray drying by using a spray dryer. Examples of a form in which a mixture of lipid membrane structures and a medicament are dispersed in an aqueous solvent include, but not particularly limited thereto, multi-lamella liposomes, unilamella liposomes, O/W type emulsions, W/O/W type emulsions, spherical micelles, fibrous micelles, layered structures of irregular shapes and the like. A size of particles (particle diameter) as the mixture, a composition of the aqueous solvent and the like are not particularly limited. For example, liposomes may have a size of 50 nm to 2 µm, spherical micelles may have a size of 5 to 100 nm, and emulsions may have a particle diameter of 50 nm to 5 µm. A concentration of the mixture in the aqueous solvent is also not particularly limited. Several methods are known as methods for producing a mixture of lipid membrane structures and a medicament in the form of dispersion in an aqueous solvent. It is necessary to appropriately chose a suitable method depending on an available form of the mixture of lipid membrane structures and a medicament.

<Production Method 1>

Production Method 1 is a method of adding an aqueous solvent to the aforementioned dried mixture of lipids and a medicament and emulsifying the mixture by using an emulsifier such as homogenizer, ultrasonic emulsifier, high-pressure injection emulsifier, or the like. When it is desired to control the size (particle diameter), extrusion (extrusion filtration) can be further performed under a high pressure by using a membrane filter having uniform pore sizes. In this method, in order to prepare a dried mixture of lipids and a medicament first, it is necessary to dissolve the medicament in an organic solvent, and the method has an advantage that it can make the best utilization of interactions between the medicament and lipid membrane structures. Even when the lipid membrane structures have a layered structure, a medicament can enter into the inside of the multiple layers, and thus use of this method generally provides a higher retention ratio of the medicament in the lipid membrane structures.

<Production Method 2>

Production Method 2 is a method of adding an aqueous solvent containing a medicament to dried lipid components obtained by dissolving the lipid components in an organic solvent and evaporating the organic solvent, and emulsifying the mixture. When it is desired to control the size (particle diameter), extrusion (extrusion filtration) can be further performed under a high pressure by using a membrane filter having uniform pore sizes. This method can be used for a medicament that is hardly dissolved in an organic solvent, but can be dissolved in an aqueous solvent. When the lipid membrane structures are liposomes, they have an advantage that they can retain a medicament also in the part of internal aqueous phase.

<Production Method 3>

Production Method 3 is a method of further adding an aqueous solvent containing a medicament to lipid membrane structures such as liposomes, emulsions, micelles or layered structures already dispersed in an aqueous solvent. This method is limitedly applied to a water-soluble medicament. The addition of a medicament to already prepared lipid membrane structures is performed from the outside. Therefore, when the medicament is a polymer, the medicament cannot enter into the inside of the lipid membrane structures, and the medicament may be present in a form that it binds to the surfaces of lipid membrane structures. When liposomes are used as the lipid membrane structures, use of Production Method 3 may result in formation of a sandwich-like structure in which the medicament is sandwiched between liposome particles (generally called as a complex). An aqueous dispersion of lipid membrane structures alone is prepared beforehand in this production method. Therefore, decomposition of a medicament during the preparation need not be taken into consideration, and a control of the size (particle diameter) is also readily operated, which enables relatively easier preparation compared with Production Methods 1 and 2.

<Production Method 4>

Production Method 4 is a method of further adding an aqueous solvent containing a medicament to a dried product obtained by once producing lipid membrane structures dispersed in an aqueous solvent and then drying the same. In this method, a medicament is limited to a water-soluble medicament in the same manner as Production Method 3. A significant difference from Production Method 3 is a mode of presence of the lipid membrane structures and a medicament. That is, in Production Method 4, lipid membrane structures dispersed in an aqueous solvent are once produced and further dried to obtain a dried product, and at this stage, the lipid membrane structures are present in a state of a solid as fragments of lipid membranes. In order to allow the fragments of lipid membranes to be present in a solid state, it is preferable to use an aqueous solution of a sugar, preferably an aqueous solution of sucrose or aqueous solution of lactose, as the aqueous solvent as described above. In this method, when the aqueous solvent containing a medicament is added, hydration of the fragments of the lipid membranes present in a state of a solid quickly starts with the invasion of water, and thus the lipid membrane structures can be reconstructed. At this time, a structure of a form in which a medicament is retained in the inside of the lipid membrane structures can be produced.

In Production Method 3, when a medicament is a polymer, the medicament cannot enter into the inside of the lipid membrane structures, and is present in a mode that it binds to the surfaces of the lipid membrane structures. Production Method 4 significantly differs in this point. In Production Method 4, an aqueous dispersion of lipid membrane structures alone is prepared beforehand, and therefore, decomposition of the medicament during the emulsification need not be taken into consideration, and a control of the size (particle diameter) is also easy attainable. For this reason, said method enables relatively easier preparation compared with Production Methods 1 and 2. Besides the above mentioned advantages, this method also has advantages that storage stability for a pharmaceutical preparation is easily secure, because the method uses lyophilization or spray drying; when the dried preparation is rehydrated with an aqueous solution of a medicament, original size (particle diameter) can be reproduced; when a polymer medicament is used, the medicament can be easily retained in the inside of the lipid membrane structures and the like.

As other method for producing a mixture of lipid membrane structures and a medicament in a form of a dispersion in an aqueous solvent, a method well known as that for producing liposomes, e.g., the reverse phase evaporation method or the like, may be separately used. When it is desired to control the size (particle diameter), extrusion (extrusion filtration) can be performed under a high pressure by using a membrane filter having uniform pore sizes. Further, examples of the method for further drying a dispersion, in which the aforementioned mixture of lipid membrane structures and a medicament is dispersed in an aqueous solvent, include lyophilization and spray drying. As the aqueous solvent in this process, it is preferable to use an aqueous solution of a sugar, preferably an aqueous solution of sucrose or an aqueous solution of lactose. Examples of the method for further freezing a dispersion, in which the aforementioned mixture of lipid membrane structures and a medicament is dispersed in an aqueous solvent, include ordinary freezing methods. As the aqueous solvent in this process, it is preferable to use an aqueous solution of sugar or aqueous solution of polyhydric alcohol in the same manner as the solution for the lipid membrane structures alone.

Lipids that can be added to the pharmaceutical composition may be suitably chosen depending on a type of a medicament to be used and the like. The lipids are used in an amount of, for example, 0.1 to 1000 parts by mass, preferably 0.5 to 200 parts by mass, based on 1 part by mass of a medicament when the medicament is not a gene. When the medicament is a gene, the amount is preferably 1 to 500 nmol, more preferably 10 to 200 nmol, with 1 µg of a medicament (gene).

The method for use of the pharmaceutical composition of the present invention which contains the lipid membrane structures may be suitably considered depending on a form thereof. The administration route for humans is not particularly limited, and either oral administration or parenteral administration may be used. Examples of dosage forms for oral administration include, for example, tablets, powders, granules, syrups, capsules, solutions for internal use and the like, and examples of dosage forms for parenteral administration include, for example, injections, drip infusion, eye drops, ointments, suppositories, suspensions, cataplasms, lotions, aerosols, plasters and the like. In the medicinal field, injections or drip infusion is preferred among them, and as the administration method, intravenous injection, subcutaneous injection and intradermal injection, as well as local injection to targeted cells or organs are preferred. Further, as for the cosmetic field, examples of forms of cosmetics include lotions, creams, toilet water, milky lotions, foams, foundations, lipsticks, packs, skin cleaning agents, shampoos, rinses, conditioners, hair tonics, hair liquids, hair creams and the like.

EXAMPLES

The present invention will be explained more specifically with reference to the following examples. However, the scope of the present invention is not limited to these examples.

Preparation Example 1

Preparation of Copolymer (CP)

The following compounds were dissolved in 1 L of toluene in a 2-L flask equipped with a stirrer and a cooling pipe and heated at 80±2° C. for 7 hours under a nitrogen atmosphere to perform the polymerization reaction.

| | |
|---|---|
| $CH_2=CHCH_2O(C_2H_4O)_{11}CH_3$ | 556 g (1.0 mol) |
| Maleic anhydride | 103 g (1.05 mol) |
| tert-Butylperoxy-2-ethyl hexanoate | 4.3 g (0.02 mol) |

Then, toluene and unreacted maleic anhydride were evaporated at 100±10° C. under a reduced pressure of 1.3 to 4.0 kPa to obtain 528 g of copolymer No. 1. The obtained copolymer No. 1 was a clear brown liquid, and had a kinematic viscosity of 206 cSt at 100° C. and a saponification value of 182 KOH mg/g.

Preparation Example 2

The following compounds were dissolved in 2 L of toluene in a 5-L flask equipped with a stirrer and a cooling pipe and heated at 80±2° C. for 9 hours under a nitrogen atmosphere to perform the polymerization reaction.

| | |
|---|---|
| $CH_2=CHCH_2O(C_2H_4O)_{33}CH_3$ | 1524 g (1.0 mol) |
| Maleic anhydride | 103 g (1.05 mol) |
| tert-Butylperoxy-2-ethyl hexanoate | 10.8 g (0.05 mol) |

Then, toluene and unreacted maleic anhydride were evaporated at 100±10° C. under a reduced pressure of 1.3 to 4.0 kPa to obtain 1518 g of copolymer No. 2. The obtained copolymer No. 2 was a brown solid at 25° C., and had a saponification value of 49.2 KOH mg/g.

Preparation Examples 3 to 8

The compounds represented by the formula (1) shown in Table 1 as well as maleic anhydride and catalysts shown in Table 2 were used to prepare copolymers Nos. 3 to 8 in the same manner as in Preparation Example 2 except that the molar ratios were changed as shown in Tables 1 and 2. Characteristics of the copolymers Nos. 3 to 8 such as mass average molecular weight, saponification value, shape, and solubility in organic solvents are shown in Table 3.

TABLE 1

| | Alkenyl ether represented by the formula (1) | | | |
|---|---|---|---|---|
| Copolymer | Type (structural formula) | Molar ratio | OE* | Molecular weight |
| No. 1 | $CH_2=CHCH_2O(C_2H_4O)_{11}CH_3$ | 1.0 | 100 | 556 |
| No. 2 | $CH_2=CHCH_2O(C_2H_4O)_{33}CH_3$ | 1.0 | 100 | 1524 |
| No. 3 | $CH_2=CHCH_2O(C_2H_4O)_6CH_3$ | 1.0 | 100 | 336 |
| No. 4 | $CH_2=C(CH_3)CH_2O(C_2H_4O)_{44}CH_3$ | 1.0 | 100 | 2022 |
| No. 5 | $CH_2=CHCH_2O\{(C_2H_4O)_{20}(C_3H_6O)_{10}\}CH_3$ | 1.0 | 100 | 1532 |
| No. 6 | $CH_2=CHCH_2O(C_3H_6O)_{10}(C_2H_4O)_{20}CH_3$ | 1.0 | 60 | 1532 |
| No. 7 | $CH_2=CHCH_2O(C_2H_4O)_{33}CH_3$ | 0.5 | 100 | 1524 |
| | $CH_2=CHCH_2O\{(C_2H_4O)_{20}(C_3H_6O)_{10}\}CH_3$ | 0.5 | 60 | 1532 |
| No. 8 | $CH_2=CHCH_2O(C_2H_4O)_{33}C_{16}H_{33}$ | 0.2 | 100 | 1734 |
| | $CH_2=CHCH_2O(C_2H_4O)_{33}CH_3$ | 0.8 | 100 | 1524 |

*Proportion of oxyethylene groups (% by mass)

Note:
The portion in { } is a random adduct.

TABLE 2

| Copolymer | Maleic anhydride Mole | Catalyst Type | Catalyst Mole |
|---|---|---|---|
| No. 1 | 1.05 | tBEH | 0.02 |
| No. 2 | 1.05 | tBEH | 0.05 |
| No. 3 | 1.05 | tBEH | 0.01 |
| No. 4 | 1.05 | tBEH | 0.05 |
| No. 5 | 1.0 | LPO | 0.03 |
| No. 6 | 1.0 | LPO | 0.03 |
| No. 7 | 1.0 | BPO | 0.07 |
| No. 8 | 1.0 | tBEH | 0.05 |

BPO: Benzoyl peroxide
LPO: Lauroyl peroxide
t-BEH: tert-Butylperoxy-2-ethyl hexanoate

TABLE 3

| Copolymer | Mass average molecular weight | Saponification value | Phase 20° C. | Phase 100° C. | Solubility Water | Solubility Acetone | Solubility Toluene |
|---|---|---|---|---|---|---|---|
| No. 1 | 22,000 | 182.0 | Liquid | Liquid | Soluble | Soluble | Soluble |
| No. 2 | 21,000 | 73.3 | Solid | Liquid | Soluble | Soluble | Soluble |
| No. 3 | 23,000 | 233.2 | Liquid | Liquid | Soluble | Soluble | Soluble |
| No. 4 | 91,000 | 49.2 | Solid | Liquid | Soluble | Soluble | Soluble |
| No. 5 | 21,000 | 64.5 | Liquid | Liquid | Soluble | Hardly soluble | Soluble |
| No. 6 | 21,000 | 61.9 | Liquid | Liquid | Soluble | Hardly soluble | Soluble |
| No. 7 | 17,000 | 71.1 | Solid | Liquid | Hardly soluble | Hardly soluble | Soluble |
| No. 8 | 16,000 | 62.0 | Solid | Liquid | Hardly soluble | Hardly soluble | Soluble |

Example 1

Synthesis of Copolymer No.
1-distearoylphosphatidylethanolamine (1 mol)
Adduct

In an amount of 748 mg (1 mmol) of distearoylphosphatidylethanolamine was added with 50 mL of toluene in a 100-mL flask equipped with a stirrer, stirred at 40° C., further added with 82 mg (1 mmol) of sodium acetate, added with 21.9 g (0.98 mmol) of the copolymer No. 1 and reacted at 40° C. for 5 hours. Completion of the reaction was confirmed by TLC as a point at which distearoylphosphatidylethanolamine came to be no longer detected by ninhydrin coloration. The reaction mixture was cooled and then filtered to remove unreacted distearoylphosphatidylethanolamine and sodium acetate, and toluene was evaporated under reduced pressure to obtain 19.8 g of copolymer No. 1-distearoylphosphatidylethanolamine.

The product was identified by thin layer chromatography (TLC) using a silica gel plate. A mixed solvent of chloroform and methanol at a mixing volume ratio of 85:15 was used as the developing solvent. Coloration was attained with iodine vapor, and contained substances were quantified by comparison with known amounts of standard substances. The spot of distearoylphosphatidylethanolamine exhibiting an Rf value of around 0.05 in TLC disappeared. The product was confirmed on the basis of disappearance of the peak of the amino group at 2960 cm$^{-1}$ and appearance of the peak of the secondary amide newly observed at 1740 cm$^{-1}$ in the IR spectrum due to the binding of the amino group of phosphatidylethanolamine and the copolymer No. 1 via an amide bond.

Example 2

Synthesis of Copolymer No.
1-distearoylphosphatidylethanolamine (2 mol)
Adduct

In an amount of 748 mg (1 mmol) of distearoylphosphatidylethanolamine was added with 50 mL of toluene in a 100-mL flask equipped with a stirrer, stirred at 40° C., further added with 82 mg (1 mmol) of sodium acetate, added with 11.0 g (0.5 mmol) of the copolymer No. 1 and reacted at 40° C. for 5 hours. Completion of the reaction was confirmed by TLC described below as a point at which distearoylphosphatidylethanolamine came to be no longer detected by ninhydrin coloration. The reaction mixture was cooled and then filtered to remove unreacted distearoylphosphatidylethanolamine and sodium acetate, and toluene was evaporated under reduced pressure to obtain 10.4 g of copolymer No. 1-distearoylphosphatidylethanolamine.

The product was identified by thin layer chromatography (TLC) using a silica gel plate. A mixed solvent of chloroform and methanol at a mixing volume ratio of 85:15 was used as the developing solvent. Coloration was attained with iodine vapor, and contained substances were quantified by comparison with known amounts of standard substances. The spot of distearoylphosphatidylethanolamine exhibiting an Rf value of around 0.05 in TLC disappeared. The product was confirmed on the basis of disappearance of the peak of the amino group at 2960 cm$^{-1}$ and appearance of the peak of the secondary amide newly observed at 1740 cm$^{-1}$ in the IR spectrum due to the binding of the amino group of phosphatidylethanolamine and copolymer No. 1 via an amide bond.

Example 3

Synthesis of Copolymer No.
2-distearoylphosphatidylethanolamine (1 mol)
Adduct

In an amount of 748 mg (1 mmol) of distearoylphosphatidylethanolamine was added with 50 mL of toluene in a 100-mL flask equipped with a stirrer, stirred at 40° C., further added with 82 mg (1 mmol) of sodium acetate, added with 20.9 g (0.99 mmol) of the copolymer No. 2 and reacted at 40°

C. for 5 hours. Completion of the reaction was confirmed by TLC described below as a point at which distearoylphosphatidylethanolamine came to be no longer detected by ninhydrin coloration. The reaction mixture was cooled and then filtered to remove unreacted distearoylphosphatidylethanolamine and sodium acetate, and toluene was evaporated under reduced pressure. Then, the residue was added with 20 mL of toluene, dissolved and added dropwise to 100 mL of hexane to obtain crystals of copolymer No. 2-distearoylphosphatidylethanolamine. The crystals were collected by filtration and vacuum-dried to obtain 19.3 g of dry crystals of the objective substance.

The product was identified by thin layer chromatography (TLC) using a silica gel plate. A mixed solvent of chloroform and methanol at a mixing volume ratio of 85:15 was used as the developing solvent. Coloration was attained with iodine vapor, and contained substances were quantified by comparison with known amounts of standard substances. The spot of distearoylphosphatidylethanolamine exhibiting an Rf value of around 0.05 in TLC disappeared. The product was confirmed on the basis of disappearance of the peak of the amino group at 2960 $cm^{-1}$ and appearance of the peak of the secondary amide newly observed at 1740 $cm^{-1}$ in the IR spectrum due to binding of the amino group of phosphatidylethanolamine and the copolymer No. 1 via an amide bond.

Example 4

Synthesis of Copolymer No.
2-distearoylphosphatidylethanolamine (2 mol)
Adduct

In an amount of 748 mg (1 mmol) of distearoylphosphatidylethanolamine was added with 50 mL of toluene in a 100-mL flask equipped with a stirrer, stirred at 40° C., further added with 82 mg (1 mmol) of sodium acetate, added with 10.5 g (0.5 mmol) of the copolymer No. 2 and reacted at 40° C. for 5 hours. Completion of the reaction was confirmed by TLC described below as a point at which distearoylphosphatidylethanolamine came to be no longer detected by ninhydrin coloration. The reaction mixture was cooled and then filtered to remove unreacted distearoylphosphatidylethanolamine and sodium acetate, and toluene was evaporated under reduced pressure. Then, the residue was added with 20 mL of toluene, dissolved and added dropwise to 100 mL of hexane to obtain crystals of copolymer No. 2-distearoylphosphatidylethanolamine. The crystals were collected by filtration and vacuum-dried to obtain 10.0 g of dry crystals of the objective substance.

The product was identified by thin layer chromatography (TLC) using a silica gel plate. A mixed solvent of chloroform and methanol at a mixing volume ratio of 85:15 was used as the developing solvent. Coloration was attained with iodine vapor, and contained substances were quantified by comparison with known amounts of standard substances. The spot of distearoylphosphatidylethanolamine exhibiting an Rf value of around 0.05 in TLC disappeared. The product was confirmed on the basis of disappearance of the peak of the amino group at 2960 $cm^{-1}$ and appearance of the peak of the secondary amide newly observed at 1740 $cm^{-1}$ in the IR spectrum due to the binding of the amino group of phosphatidylethanolamine and the copolymer No. 1 via an amide bond.

Example 5

Synthesis of Copolymer No.
5-distearoylphosphatidylethanolamine (2 mol)
Adduct

In an amount of 748 mg (1 mmol) of distearoylphosphatidylethanolamine was added with 50 mL of toluene in a 100-mL flask equipped with a stirrer, stirred at 40° C., further added with 82 mg (1 mmol) of sodium acetate, added with 10.4 g (0.49 mmol) of the copolymer No. 5 and reacted at 40° C. for 5 hours. Completion of the reaction was confirmed by TLC described below as a point at which distearoylphosphatidylethanolamine came to be no longer detected by ninhydrin coloration. The reaction mixture was cooled and then filtered to remove unreacted distearoylphosphatidylethanolamine and sodium acetate, and toluene was evaporated under reduced pressure to obtain 10.1 g of copolymer No. 5-distearoylphosphatidylethanolamine.

The product was identified by thin layer chromatography (TLC) using a silica gel plate. A mixed solvent of chloroform and methanol at a mixing volume ratio of 85:15 was used as the developing solvent. Coloration was attained with iodine vapor, and contained substances were quantified by comparison with known amounts of standard substances. The spot of distearoylphosphatidylethanolamine exhibiting an Rf value of around 0.05 in TLC disappeared. The product was confirmed on the basis of disappearance of the peak of the amino group at 2960 $cm^{-1}$ and appearance of the peak of the secondary amide newly observed at 1740 $cm^{-1}$ in the IR spectrum due to the binding of the amino group of phosphatidylethanolamine and the copolymer No. 1 via an amide bond.

Example 6

Synthesis of Copolymer No.
5-distearoylphosphatidylethanolamine (1 mol)
Adduct

In an amount of 748 mg (1 mmol) of distearoylphosphatidylethanolamine was added with 50 mL of toluene in a 100-mL flask equipped with a stirrer, stirred at 40° C., further added with 82 mg (1 mmol) of sodium acetate, added with 90.9 g (0.99 mmol) of the copolymer No. 4 and reacted at 40° C. for 8 hours. Completion of the reaction was confirmed by TLC described below as a point at which distearoylphosphatidylethanolamine came to be no longer detected by ninhydrin coloration. The reaction mixture was cooled and then filtered to remove unreacted distearoylphosphatidylethanolamine and sodium acetate, and toluene was evaporated under reduced pressure to obtain 85.4 g of copolymer No. 4-distearoylphosphatidylethanolamine.

The product was identified by thin layer chromatography (TLC) using a silica gel plate. A mixed solvent of chloroform and methanol at a mixing volume ratio of 85:15 was used as the developing solvent. Coloration was attained with iodine vapor, and contained substances were quantified by comparison with known amounts of standard substances. The spot of distearoylphosphatidylethanolamine exhibiting an Rf value of around 0.05 in TLC disappeared. The product was confirmed on the basis of disappearance of the peak of the amino group at 2960 $cm^{-1}$ and appearance of the peak of the secondary amide newly observed at 1740 $cm^{-1}$ in IR spectrum due to the binding of the amino group of phosphatidylethanolamine and the copolymer No. 1 via an amide bond.

Example 7

Preparation of Skin Toner (Evaluation as Solubilizer)

A skin toner was prepared by using the copolymer No. 5-distearoylphosphatidylethanolamine (1 mol) adduct of Synthesis Example 6. Among the base materials in the composition shown in Table 4, glycerin and propylene glycol were added to purified water and uniformly dissolved. Other base materials were added to ethanol, and the mixture was made uniform, then added to the aforementioned purified water phase with stirring and solubilized to obtain a skin toner.

TABLE 4

| | |
|---|---|
| Propylene glycol | 5.0 wt % |
| Glycerin | 2.0 wt % |
| Octadecyl alcohol | 0.5 wt % |
| Hydrogenated soybean lecithin | 0.5 wt % |
| Ethanol | 7.0 wt % |
| Copolymer No. 5-distearoylphosphatidylethanolamine (1 mol) adduct | 2.0 wt % |
| Tocopherol | 0.02 wt % |
| Perfume | As required |
| Preservative | As required |
| Purified water | 73.0 wt % |

Example 8

Preparation of Liposome Emulsion (Evaluation as Dispersing Agent for Cosmetics)

Method for Preparing Liposomes

In an amount of 645 mg of hydrogenated soybean phosphatidylcholine, 299 mg of cholesterol, 23 mg of myristic acid (molar ratio: 1:1:0.1) and the copolymer No. 2-distearoylphosphatidylethanolamine (1 mol) adduct were added so that the mixed lipid concentration should become 5% by mole, added with 10 to 11 mL of physiological saline heated at 60° C. beforehand so that the mixed lipid concentration was 10% by mass and stirred, and further mixed by using a homogenizer on a water bath at 60° C. for 10 minutes to obtain a liposome solution. Among the base materials of the composition shown in Table 5, those of the oil phase containing an emulsifier were heated at 60° C. and uniformly dissolved, and those of the aqueous phase using the liposome solution were added at the same temperature with stirring to obtain a liposome emulsion.

TABLE 5

| | |
|---|---|
| Oil phase: | |
| Hexadecyl alcohol | 2.0 wt % |
| Vaseline | 2.0 wt % |
| Squalane | 5.0 wt % |
| Liquid paraffin | 10.0 wt % |
| Polyoxyethylene monooleic acid ester | 2.0 wt % |
| Tocopherol | 0.02 wt % |
| Perfume | As required |
| Preservative | As required |
| Aqueous phase: | |
| Propylene glycol | 2.0 wt % |
| Purified water | 67.0 wt % |
| Liposome solution | 10.0 wt % |

Example 9

Evaluation as Liposome Capable of Long-term Residence in Blood (1) Preparation of Liposomes Each of the lipids mentioned in each of the membrane compositions shown in Table 6 (Formulation Examples 1 to 6, Control Examples 1 to 2) were weighed in each ratio and dissolved in a chloroform/methanol mixture (2:1), then the organic solvents were evaporated by using an evaporator, and further the residue was dried under reduced pressure for 1 hour. Then, the dried lipids (lipid film) were added with 10 mL of 155 mM aqueous ammonium sulfate (pH 5.5) heated at 65° C. beforehand, and the mixture was lightly stirred by using a vortex mixer on a hot water bath (until lipid was substantially peeled off from a recovery flask). This lipid dispersion was transferred to a homogenizer, homogenized for 10 strokes and sized by using polycarbonate membrane filters with various pore sizes (0.2 μm×3 times, 0.1 μm×3 times, 0.05 μm×3 times and 0.03 μm×3 times) to prepare a dispersion of empty liposomes having a particle diameter of about 100 nm.

In an amount of 4 mL of this empty liposome dispersion was diluted 2.5 times with physiological saline, and the resulting diluted liposome dispersion was placed in an ultracentrifugation tube and centrifuged at 65,000 rpm for 1 hour. Then, the supernatant was discarded, and the precipitates were resuspended in physiological saline to make the dispersion volume 10 mL, the volume of the liposome dispersion before the centrifugation (at this time point, the total lipid concentration was adjusted to 50 mM). The aforementioned empty liposome dispersion in which the external aqueous phase was replaced with physiological saline (total lipid concentration: 50 mM) and a doxorubicin solution (medicament concentration: 3.3 mg/mL physiological saline) were heated beforehand at 60° C., and the empty liposome dispersion and the doxorubicin solution were added at a volume ratio of 4:6 (final medicament concentration: 2.0 mg/mL, final lipid concentration, 20 mM) and incubated at 60° C. for 1 hour. Subsequently, the mixture was cooled to room temperature to obtain a doxorubicin-containing liposome dispersion.

(2) Physical Properties of the Liposome

The percentage of doxorubicin retained by the liposomes was obtained by collecting a part of the aforementioned liposome dispersion, subjecting the sample to gel filtration (Sephadex G-50, mobile phase was physiological saline), and then quantifying doxorubicin in the liposome fraction eluted in the void volume by using liquid chromatography. Further, particle diameter was determined by measurement based on the quasi-elastic light scattering (QELS) method performed for a part of the aforementioned liposome dispersion. As a result, the percentage of doxorubicin, the active ingredient retained by liposomes, was almost 100% in liposomes except for those of Formulation Examples 4 and 5 as shown in Table 6. Therefore each original liposome dispersion was used without any treatment, and diluted 4/3 times with physiological saline for the blood residence experiment in rats described below (final medicament concentration: 1.5 mg/mL, final lipid concentration: 15 mM). Further, the liposomes of Formulation Examples 4 and 5 were subjected to ultracentrifugation (65,000 rpm, 1 hour) to remove unencapsulated medicament in the supernatant and then reconstituted with physiological saline so that a final medicament concentration of 1.5 mg/mL was obtained (final lipid concentrations of Prescription Examples 4 and 5 were about 17.2 mM and about 17.9 mM, respectively). The particle diameters of the liposomes were 50 to 100 nm for the both examples.

(3) Experiment for Evaluating Blood Residence in Rats

An experiment for evaluating blood residence was performed in SD male rats (6-week old) using Formulation Examples 1 to 6 and Control Examples 1 to 2 mentioned above. Each liposome dispersion was administered to rats from the cervical vein under ether anesthesia (each group consisted of 5 animals, dose: 7.5 mg doxorubicin/5 mL/kg), then blood was collected in heparin (0.5 to 1 mL) from the cervical vein under ether anesthesia at each blood collection time (2, 4, 8, 24, 48, 72, 120, 168 hours) and subjected to plasma skimming. Then, in a conventional manner, the blood was pretreated, and plasma medicament concentration was measured by HPLC. The AUC (0 to ∞) was calculated from the plasma medicament concentration obtained with each formulation of liposome dispersion according to the trapezoidal rule. As shown in Table 6, AUCs larger by 1 order or more were obtained with the liposome formulations containing the phospholipid derivatives of the present invention (Formulation Examples 1 to 6) compared with AUCs obtained with the liposomes of Control Example 1 not containing the lipid derivative of the present invention or the liposomes of Control Example 2 added only with the phospholipid portion (DSPE: distearoylphosphatidylethanolamine) of the lipid derivative of the present invention, and thus clearly longer residence in the blood was observed with the liposome formulations containing the phospholipid derivatives of the present invention.

What is claimed is:

1. A phospholipid derivative, which is a phospholipid and is a copolymer containing, as essential component units, (A) a component unit A represented by the following formula (1), (B) a component unit B represented by the following formula (2A) and/or the following formula (2B), and (C) a component unit C represented by the following formula (3):

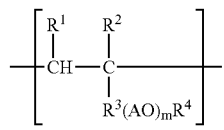

(1)

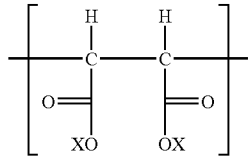

(2A)

TABLE 6

| | Liposome membrane composition | Particle size (nm) | Percentage of carried active ingredient (%) | Mean $AUC_{0,\infty} \pm SD$ (μg · hr/mL) |
|---|---|---|---|---|
| Formulation Example 1 | DSPE1-AKM0531/HSPC/Cholesterol = 0.104 mM/11.28 mM/7.68 mM | 89 | 100.0 | 3877 ± 308 |
| Formulation Example 2 | DSPE1-AKM0531/HSPC/Cholesterol = 0.520 mM/11.28 mM/7.68 mM | 92 | 93.4 | 4191 ± 388 (n = 4) |
| Formulation Example 3 | DSPE1-AKM0531/HSPC/Cholesterol = 1.04 mM/11.28 mM/7.68 mM | 55 | 100.0 | 3064 ± 413 |
| Formulation Example 4 | DSPE1-AKM0350/HSPC/Cholesterol = 0.104 mM/11.28 mM/7.68 mM | 49 | 87.4 | 2809 ± 288 |
| Formulation Example 5 | DSPE2-AKM0350/HSPC/Cholesterol = 0.104 mM/11.28 mM/7.68 mM | 52 | 83.9 | 3063 ± 181 |
| Formulation Example 6 | DSPE1-AKM1511/HSPC/Cholesterol = 1.04 mM/11.28 mM/7.68 mM | 72 | 99.5 | 1918 ± 74 |
| Control Example 1 | HSPC/Cholesterol = 11.90 mM/8.10 mM | 91 | 100.0 | 452 ± 98 |
| Control Example 2 | DSPE/HSPC/Cholesterol = 1.04 mM/11.28 mM/7.68 mM | 94 | 100.0 | 397 ± 133 |

Note:
DSPE1-AKM0531 → Molecular weight of PEG chain = 500, k = 30, 1 mol of DSPE per 30 mol of k
DSPE1-AKM0350 → Molecular weight of PEG chain = 300, k = 50, 1 mol of DSPE per 50 mol of k
DSPE2-AKM0350 → Molecular weight of PEG chain = 300, k = 50, 2 mol of DSPE per 50 mol of k
DSPE1-AKM1511 → Molecular weight of PEG chain = 1500, k = 10, 1 mol of DSPE per 10 mol of k
HSPC: Hydrogenated soybean phosphatidylcholine
$k = k^I + k^{II}$

INDUSTRIAL APPLICABILITY

The phospholipid derivative of the present invention is highly safe for living bodies and useful as a surfactant, solubilizer, or dispersing agent in the fields of cosmetics and the like. Further, the phospholipid derivative of the present invention can be used for preparation of lipid membrane structures such as liposomes, and a lipid membrane structure containing the phospholipid derivative of the present invention, preferably liposome, is characterized to have a longer circulating time in blood.

-continued

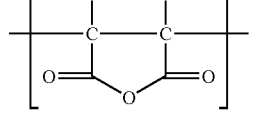

(2B)

-continued

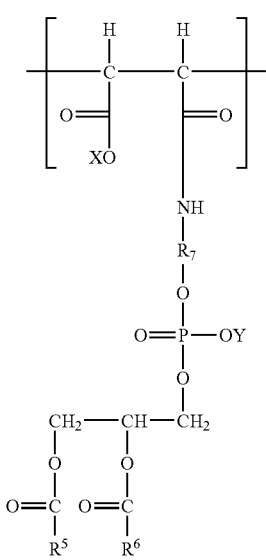

(3)

wherein, in the formula (1), $R^1$ and $R^2$ independently represent hydrogen atom or methyl group, provided that $R^1$ and $R^2$ do not simultaneously represent methyl group; $R^3$ represents a divalent hydrocarbon group having 1 to 3 carbon atoms; AO independently represents an oxyalkylene group having 2 to 4 carbon atoms; m represents an average molar number of the added oxyalkylene groups and is a number in the range represented as $4 \leq m \leq 100$; and $R^4$ represents hydrogen atom, a hydrocarbon group having 1 to 20 carbon atoms or an acyl group having 1 to 20 carbon atoms; in the formula (2A), X independently represents hydrogen atom, an alkali metal atom, ammonium or an organic ammonium; and in the formula (3), $R^5CO$ and $R^6CO$ independently represent an acyl group having 8 to 24 carbon atoms; $R^7$ represents a divalent hydrocarbon group having 2 to 4 carbon atoms; X represents hydrogen atom, an alkali metal atom, ammonium or an organic ammonium, and Y represents hydrogen atom, an alkali metal atom ammonium or an organic ammonium, wherein a molar ratio of the component unit A relative to a total of the component unit B and the component unit C is from 7/3 to 3/7, and the component unit C is contained at a ratio of from 1 to 5 moles per 1 mole of the copolymer.

2. The phospholipid derivative according to claim 1, wherein the total number of the component unit(s) A, the component unit(s) B, and the component unit(s) C contained in the copolymer is 3 or more and 150 or less.

3. The phospholipid derivative according to claim 1, wherein the total number of the component unit(s) A, the component unit(s) B, and the component unit(s) C contained in the copolymer is 5 or more and 50 or less.

4. The phospholipid derivative according to claim 1, wherein $R^1$ is hydrogen atom, $R^2$ is hydrogen atom or methyl group, and $R^3$ is methylene group.

5. The phospholipid derivative according to claim 1, wherein $R^7$ is ethylene group.

6. A surfactant comprising the phospholipid derivative according to claim 1.

7. A lipid membrane structure comprising the phospholipid derivative according to claim 1.

8. The lipid membrane structure according to claim 7, which is a liposome.

9. A pharmaceutical composition containing the lipid membrane structure according to claim 7 retaining a medicament.

10. The pharmaceutical composition according to claim 9, wherein the medicament is an antitumor agent.

11. A method for producing the phospholipid derivative according to claim 1, which comprises the step of reacting a copolymer containing the component unit A and the component unit B at a molar ratio of from 7/3 to 3/7 with a compound represented by the following formula (4):

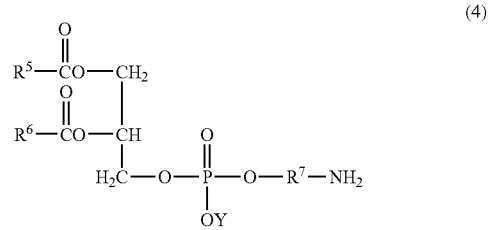

(4)

wherein $R^5CO$, $R^6CO$, $R^7$, and Y have the same meanings as defined above.

* * * * *